United States Patent
Riffle et al.

(10) Patent No.: US 6,749,844 B2
(45) Date of Patent: Jun. 15, 2004

(54) MAGNETIC FLUIDS

(75) Inventors: Judy S. Riffle, Blacksburg, VA (US); Janice Paige Phillips, Blacksburg, VA (US); James P. Dailey, Erie, PA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 10/232,730

(22) Filed: Sep. 3, 2002

(65) Prior Publication Data

US 2003/0042462 A1 Mar. 6, 2003

Related U.S. Application Data (60) Division of application No. 09/342,885, filed on Jun. 29, 1999, which is a continuation-in-part of application No. 09/075,698, filed on May 11, 1998, now Pat. No. 6,135,118.
(60) Provisional application No. 60/046,171, filed on May 12, 1997.

(51) Int. Cl.$^7$ .............................................. A61K 31/74
(52) U.S. Cl. ................ 424/78.08; 600/420; 424/78.02; 424/78.04
(58) Field of Search ............................. 424/1.11, 1.65, 424/9.3, 9.322, 78.02, 78.04, 78.08, 78.17; 600/410, 420

(56) References Cited

U.S. PATENT DOCUMENTS 6,135,118 A * 10/2000 Dailey ........................ 128/898
6,464,968 B2 * 10/2002 Riffle ....................... 424/78.02

OTHER PUBLICATIONS

Dailey et al.; "Synthesis of silicone magnetic fluids for use in eye surgery"; Journal of Magnetism and Magnetic Materials; No. 194, pp. 140–148; 1999.

Griffiths et al.; "The structure, magnetice characterization, and oxidation of colloidal iron dispersions"; J. Appl. Phys. No. 50(11); pp. 7108–7115; Nov. 1979.

Hess et al.; "Polymers for stabilization of colloidal cobalt particles"; Journal of Applied Polymer Science; No. 10; pp. 1915–1927; 1966.

Kilner et al.; "Preparation and properties of metallic iron ferrofluids"; IEE Transactions on Magnetics; vol. 20, No. 5, Pt. 2; pp. 1735–1737; Sep. 1984.

Lambrick et al.; "Preparation and properties of Ni–Fe magnetic fluids"; Journal of Magnetism and Magnetic Materials; No. 65, pp. 257–260; 1987.

Li et al.; "Polydimethylsilexane–b–Poly (3–cyanopropyl) methylsiexane–b–Polydimethylsiloxane Triblock Suspension Stabilizers"; Polymer Preprints, Division of Polymer Chemistry, American Chemical Society; vol. 37, No. 2, pp. 660–661; Aug., 1996.

Nakatani et al.; "Preparation and magnetic properties of colloidal ferromagnetic metals"; Journal of Magnetism and Magnetic Materials, No 65; pp 261–264; 1987.

Papirer et al.; "The preparation of a ferrofluid by decomposition of dicolbalt octacarbonyl—I. Experimental parameenters"; Journal of Colloid and Interface Science, No 94(1); pp. 207–219; 1983.

Papirer et al.; "The preparation of a ferrofluid by decomposition of dicolbalt octacarbonyl—II. Nucleation and growth of particles"; Journal of Colloid and Interface Science, No 94(1); pp. 220–228; 1983.

Venkatesan et al.; Polymer Reprints, vol. 36, No. 1; pp. 483–484, 1995.

* cited by examiner

*Primary Examiner*—Dameron L. Jones
(74) *Attorney, Agent, or Firm*—Whitman, Curtis & Christofferson, P.C.

(57) ABSTRACT

A magnetic fluid is provided comprising a block copolymer stabilizer, magnetic particles and a fluid polysiloxane medium. The stabilizer comprises an anchor block which chelates magnetic metal particles, and at least one end block which is compatible with the polysiloxane medium.

1 Claim, 4 Drawing Sheets

# MAGNETIC FLUIDS

CROSS REFERENCE TO RELATED APPLICATIONS

This application is a division of U.S. patent application Ser. No. 09/342,885 filed Jun. 29, 1999, which is continuation-in-part of U.S. patent application Ser. No. 09/075,698 filed May 11, 1998 now U.S. Pat. No. 6,135,118, which is based on U.S. Provisional Application Serial No. 60/046,171, filed May 12, 1997, incorporated herein by reference in full.

FIELD OF THE INVENTION

This invention relates to methods for making magnetic fluid compositions useful for treating disorders. More specifically, the invention relates to methods for synthesizing copolymers useful as magnetic dispersion stabilizers.

BACKGROUND OF THE INVENTION

The mammalian eye comprises two chambers. The anterior chamber is bounded by the cornea and lens, and contains the aqueous humor. The volume behind the lens contains the vitreous humor, with the retina attached to the back wall of the eye. The retinal layer is not firmly attached to the eye, and can become detached, resulting in eventual death of the retina and loss of vision. The retina may detach along an edge, e.g. as the result of trauma, or as the result of a tear allowing fluid to leak underneath the retina and separate the retina from the underlying choroid. Retinal detachment can be treated by means of a scleral buckle, a silicone band that encircles the eye and compresses the wall of the eye inward against the retina. Alternatively, the vitreous humor may be replaced in whole or in part with a tamponade, a heavy liquid or gas intended to flatten the retina against the choroid.

Currently used internal tamponades ($SF_6$, $C_3F_8$, silicone oil) float up, leaving the inferior retina unprotected, or sink down (fluorosilicone), leaving the superior retina unprotected. Current tamponades also fill the vitreous cavity, decreasing vision, and contact anterior chamber structures, causing cataract and glaucoma.

Stable magnetic fluids are currently known. However, the fluids are typically dispersed in organic media and contain particles that are small in size. Thus, the organic media renders them unsuitable for biomedical applications and the small particle size causes their response to low external magnetic fields to be relatively low. Larger particles tend to aggregate and subsequently precipitate using currently available stabilizers.

SUMMARY OF THE INVENTION

A new method for making compositions useful for treating retinal detachment is provided.

Another object of the invention is to provide a stable magnetic silicone fluid.

Another object of the invention is to provide methods for synthesizing copolymers suitable for use in the method of the invention.

Another object of the invention is to provide specific examples of magnetic fluid preparation.

Still another object of the invention is to provide stable, biocompatible magnetic fluids in polydimethylsiloxane fluid for use in ophthalmology.

Still another object of the invention is to provide block copolymer stabilizers that efficiently stabilize particles as large as about 17–20 nm in diameter.

Yet another object of the invention is to provide stable particles having a relatively high magnetic response to low externally applied fields.

DETAILED DESCRIPTION

Definitions

The term "magnetic fluid" as used herein refers to a biocompatible liquid having magnetic particles dispersed throughout. Magnetic fluids can be manipulated using magnetic fields.

The term "biocompatible" refers to materials which do not cause undue inflammation or injury when in extended contact with living tissue.

The term "effective amount" as used herein refers to an amount of magnetic fluid sufficient to hold a detached retina in place. In general, an effective amount will be the amount necessary to form a ring around the inside of the vitreal chamber having a thickness of at least about 1 mm, and a width of about 1 to about 7 mm.

The term "cross-linkable polymer" refers to a flexible plastic polymer which can be rendered rigid by addition of a crosslinking agent or catalyst.

The term "magnetic particles" refers to metallic particles that respond to magnetic fields.

The term "relatively inaccessible location" refers to a site within the body that is difficult to directly access through standard surgical techniques without undue or unacceptable damage to surround tissue. Examples of relatively inaccessible locations include intracranial regions and intraocular sites, where surgical access can carry the risk of brain damage or loss of vision.

The term "exoplant" or "localized scleral exoplant" refers to a generally flat patch that is sutured or adhered to the outer surface of the eye.

General Method

Magnetic fluids useful in the invention are preferably biocompatible. Thus, the magnetic fluid preferably comprises a non-toxic polymer carrier, such as a fluid dimethylsiloxane or trifluoropropylmethylsiloxane, a fluid siloxane containing block copolymer, a hydrogel or the like. The fluid may further comprise surfactants and/or dispersing agents to stabilize the combination of polymer and magnetic particles.

Block copolymers are often more efficient than homopolymers as dispersion stabilizers. The stabilizer comprise "anchor" blocks which strongly adsorb onto the magnetic particle surface, and "tail" blocks which protrude into the medium. The chemical structure of the "tail" block of the block copolymer stabilizer should be related to the structure of the carrier fluid such that it is soluble in the polymeric carrier fluid. Thus, for a polydimethylsiloxane carrier fluid, a preferred "tail" chemical structure of the block copolymer stabilizer is itself a polydimethylsiloxane block. Alternatively, if the carrier fluid is a poly(trifluoropropylmethylsiloxane), a preferred copolymer stabilizer might have a trifluoropropylmethylsiloxane tail block. Di- or triblock copolymers are preferred having a poly(3-cyanopropyl)methylsiloxane (PCPMS) "anchor" block bound to at least one polydimethylsiloxane (PDMS) "tail" blocks.

The volumes of stabilizer and magnetic particles can constitute any volume percentage of the magnetic fluid, but preferably comprise about 2% to about 100%, and most preferably about 10% to about 100% by volume. In cases where the block copolymer stabilizer itself is a polymeric fluid, the stabilizer can function as both the dispersion stabilizer and the carrier fluid. Thus, for stabilizers where the tail block(s) have very low glass transition temperatures (e.g., polydimethylsiloxane or polytrifluoropropylmethylsiloxane), and where the tail to anchor block weight ratio in the stabilizer is greater than about 1:1, these stabilizers will be fluid and can function as both the dispersion stabilizers and also the carrier fluids. The ratio of stabilizer to magnetic particles is from about 1:10 to about 10:1, preferably from about 10:1 to about 1:1 by weight. The remainder of the magnetic fluid comprises the non-toxic biocompatible carrier, and optionally other stabilizers and preservatives.

The block copolymer stabilizers can be made according to the method described in Riffle et al., "Polydimethylsiloxane-b-Poly(3-cyanopropyl) methylsiloxane-b-Polydimethylsiloxane Triblock Suspension Stabilizers", Polymer Preprints, August, 1996, which is incorporated by reference herein in its entirety. Alternatively, copolymer magnetic dispersion stabilizers can be made according to the exemplary methods disclosed herein (Schemes 3 and 4).

Figure 3:
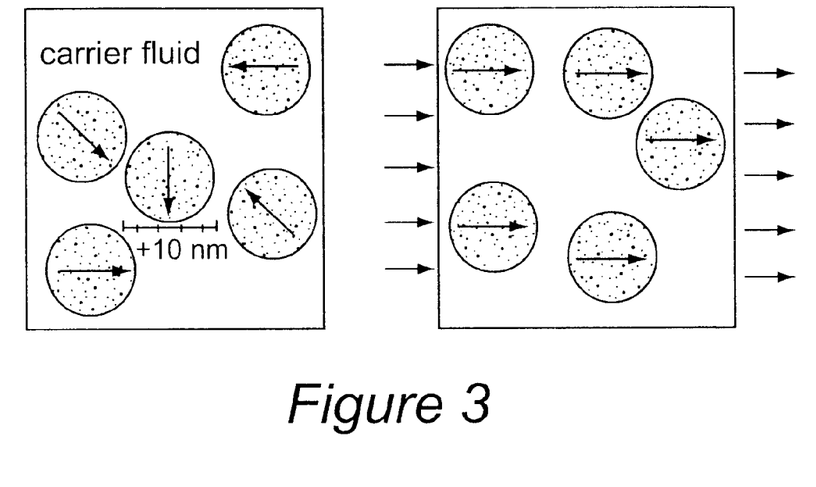
FIG. 3 is a diagrammatic view of the effect that an external magnetic field has on single domain magnetic particle in accordance with the present invention.

The magnetic particles are any ferromagnetic element or compound, including without limitation Fe, Ni, Co, iron oxides, neodymium, samarium, and the like, and are preferably about 2–20 nm in maximum diameter. Ferrofluids are suspensions of fine magnetic particles in a carrier fluid. Preferably, the medium is a polyalkylsiloxane, such as polydimethylsiloxane or poly(trifluoropropylmethylsiloxane). The magnetic particle size is so small that each particle is a single domain; that is, all of the atoms within a single particle are aligned together. In the absence of an external magnetic field, the particles are aligned randomly and are not magnetized. When an external magnetic filed is applied, the particles rotate easily to align in the field direction. These particles greatly enhance the strength of the applied field. When the external field is removed, the fluid particles again randomize their orientations, and the fluid is no longer magnetic.

The amount of stabilizer used will depend upon the concentration of magnetic particles required to hold the tamponade in place with a magnetized scleral buckle of given magnetic strength. This may be determined empirically by those of ordinary skill.

The stabilizer, comprising an anchor block which binds to metal and tail block(s) which are compatible with silicone fluid, is used to suspend magnetic particles in silicone fluid. The anchor blocks of poly(3-cyanopropyl)methylsiloxane (PCPMS) with reactive endgroups are prepared using an anionic reaction of cyclic monomers. Riffle et al., supra. The stabilizer having a PCPMS anchor block flanked by two polydimethylsiloxane (PDMS) tail blocks are formed using lithium silanolate terminated PCPMS to polymerize hexamethyltrisiloxane. Riffle et al., supra.

Scheme 1
Formation of Anchor Blocks

Scheme 2
Formation of Dispersion Stabilizer

Preparation of poly(dimethylsiloxane-b-cyanopropylmethylsiloxane-b-dimethyl-siloxane) (PDMS-b-PCPMS-b-PDMS) triblock copolymer dispersion stabilizers is illustrated in Scheme 3. 3-cyanopropylmethylcyclotetrasiloxane ($D_4CN$) is prepared by the hydrosilylation of tetramethylcyclotetrasiloxane ($D_4H$) with allyl cyanide. Dilithium diphenylsilanediolate initiator is synthesized by deprotonation of diphenylsilanediol using diphenylmethyllithium. Lithium silanolate capped PCPMS macroinitiators are prepared by equilibrium polymerization of $D_4CN$ with dilithium diphenylsilanediolate as an initiator. Finally, PDMS-b-PCPMS-b-PDMSs are obtained by a kinetically controlled polymerization of hexamethylcyclotrisiloxane ($D_3$) using the lithium silonate capped PCPMS macroinitiators.

Scheme 3

↓ equilibrium polymerization

↓ kinetically controlled polymerization

PDMS-b-PCPMS-b-PDMS
(triblock copolymer)

An alternative procedure for preparing PDMS-b-PCPMS-b-PDMS triblock copolymer dispersion stabilizers is outlined in Scheme 4. $D_4CN$ is prepared as in previous experiments by the hydrosilylation of $D_4H$ with allyl cyanide. However, the lithium silanolate capped PCPMS macroinitiators are prepared by equilibrium polymerization of $D_4CN$ with LiOH. Triblock copolymers, PDMS-b-PCPMS-b-PDMSs, are obtained by kinetically controlled polymerization of $D_3$, as above.

Scheme 4

-continued

—Fe$_2$O$_3$ powder (or other magnetic particles) is dispersed in silicone fluid containing the block copolymer stabilizers with ultrasonification. Organometallic precursors such as metal carbonyls or metal alkenes are also used in the presence of the block copolymer stabilizers to generate the stabilized magnetic particle dispersions in situ.

While not being bound to a theory, it is believed that the stabilizer produces a stable colloidal suspension because:

1. The block copolymers are strongly absorbed onto the metal surface via the central cyano-containing PCPMS "anchor" block.
2. The "tail" blocks of PDMS extend into the PDMS medium. In close proximity, the mutual repulsion of these tails causes them to extend as far as possible into the medium.
3. The particles tend not to coagulate because approach of the particle-stabilizer complexes causes an unfavored decrease in entropy.
4. Also, coagulation of the particles requires desorption or lateral surface movement of the stabilizers which is an unfavored energy requirement.

The scleral buckle comprises a flexible biocompatible material, suitable for application to the sclera. The buckle is preferably a flexible silicone band, dimensioned to fit snugly around the eye and gently compress the eye so that the inner surface of the vitreal chamber is urged into contact with the periphery of the retina. The buckle is preferably fabricated by combining medical grade siloxane with magnetic particles (as described above for the magnetic fluid) prior to cross-linking or curing. Buckles can be provided in the form of strips or rings, generally as a relatively flat band. Rings are provided in a plurality of different diameters, to accommodate eyes of different sizes. Strips can be provided in any length, and cut to fit at the time of application, followed by connecting the ends of the strip. Strips and rings are preferably cast in their final form. Scleral exoplants or patches are formed in the same way, and can optionally be provided with positioning straps.

Figure 1:
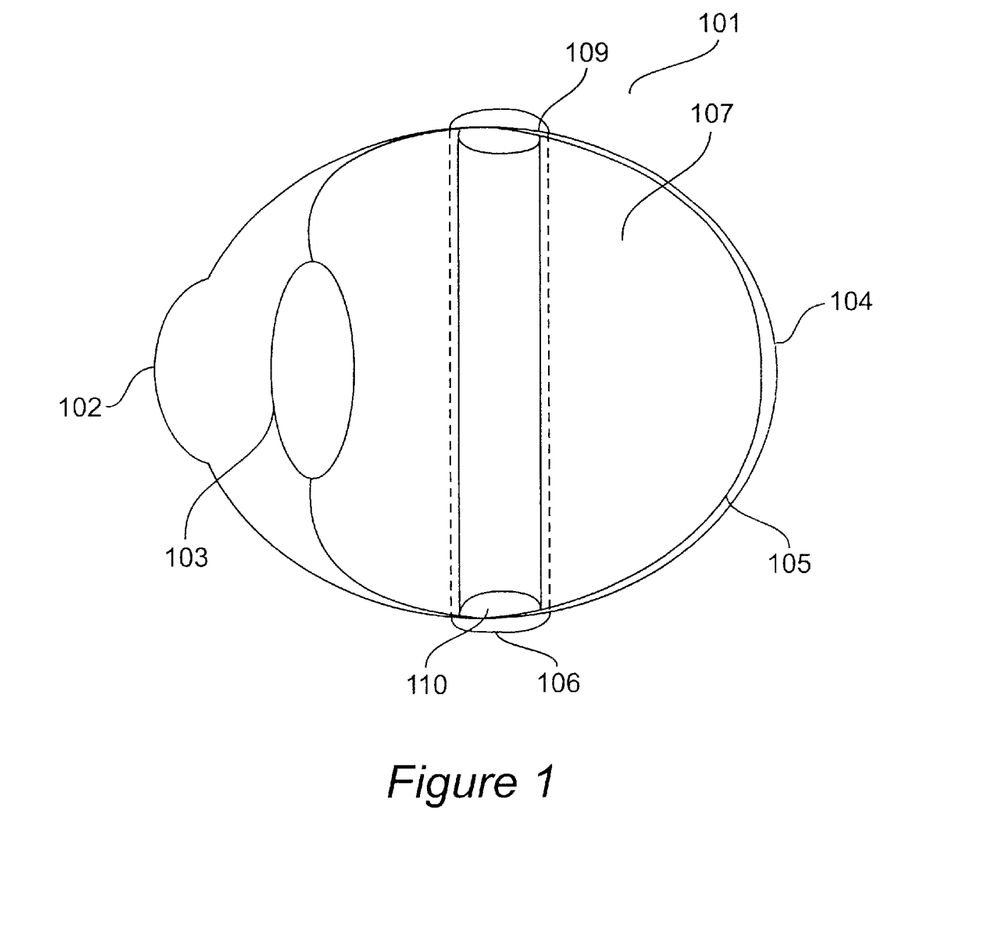
FIG. 1 is a cross-sectional view of an eye having a magnetized scleral buckle and a magnetic fluid tamponade.

FIG. 1 is a cross-sectional view of an eye 101 having cornea 102, lens 103, choroid 104, retina 105, vitreal chamber 107, magnetic scleral buckle 106 and magnetic fluid 110 of the invention. In the practice of the invention, a subject is generally first diagnosed as having retinal detachment. The method of the invention is particularly suited for treating holes along the periphery of the retina 109. The eye is first subjected to a partial or total vitrectomy (removal of part or all of the vitreous humor) by surgical methods. The magnetic fluid is applied, for example using a syringe, and the magnetic scleral buckle 106 is positioned immobilized in place, generally by suture or adhesive. The scleral buckle attracts the magnetic fluid 110 to an annular position inside the eye, closest to the retinal periphery 109.

Figure 2:
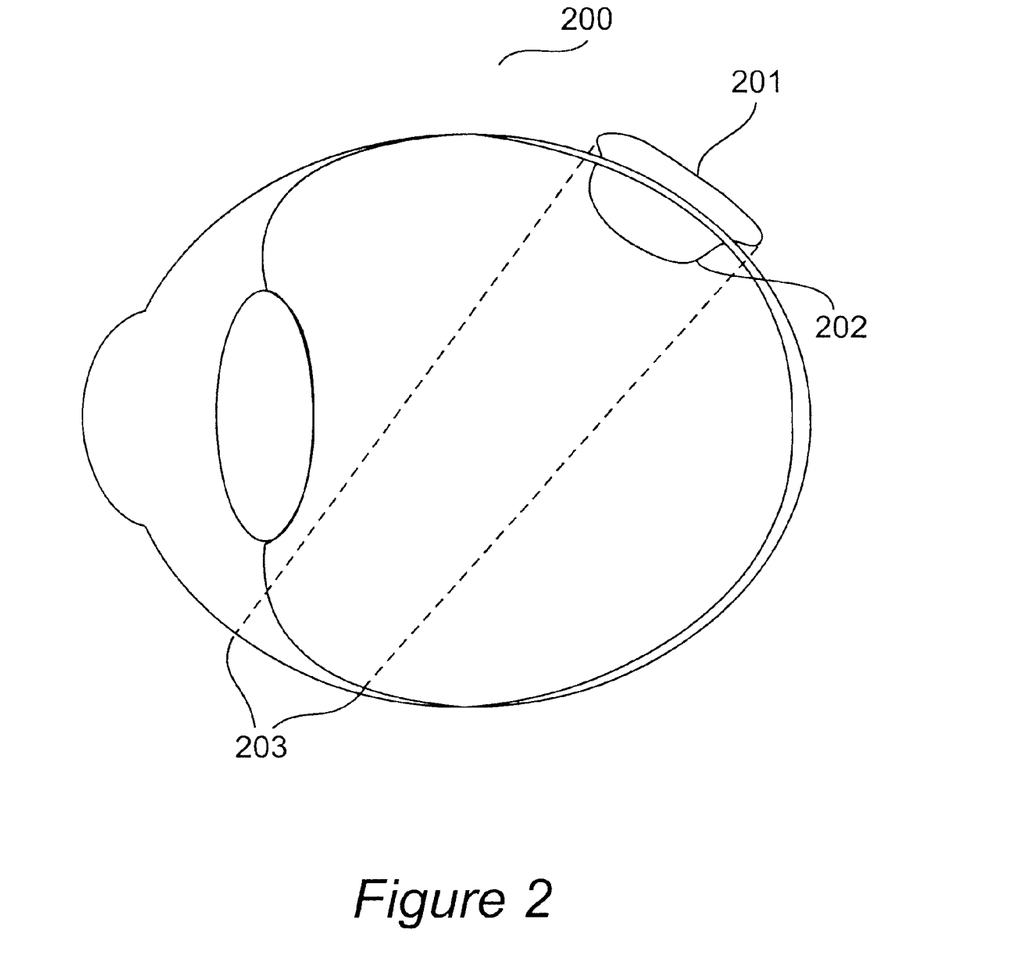
FIG. 2 is a cross-sectional view of an eye having a magnetized exoplant and magnetic fluid.

Detachments in other regions of the retina can also be treated, by positioning the scleral buckle over the detached region, or by applying a magnetized exoplant. FIG. 2 is a cross-sectional view of an eye 200 having a magnetic fluid tamponade 202 held in place by a magnetized exoplant 201. The exoplant 201 can be fixed in place using adhesive, sutures, and/or positioning bands 203. The localized exoplant is also suitable for treating intraocular tumors, when used in combination with a magnetic fluid 202 containing a chemotherapeutic or radiotherapeutic agent. Further, one can employ an exoplant to shield the macula from radiation damage during cancer treatment by applying an exoplant to the sclera such that magnetic fluid injected into the vitreous chamber covers the macula. The magnetic fluid partially shields the macula from the effects of radiation, which may otherwise lead to radiation retinopathy. The exoplant and fluid can be removed at the conclusion of treatment.

Figure 4:
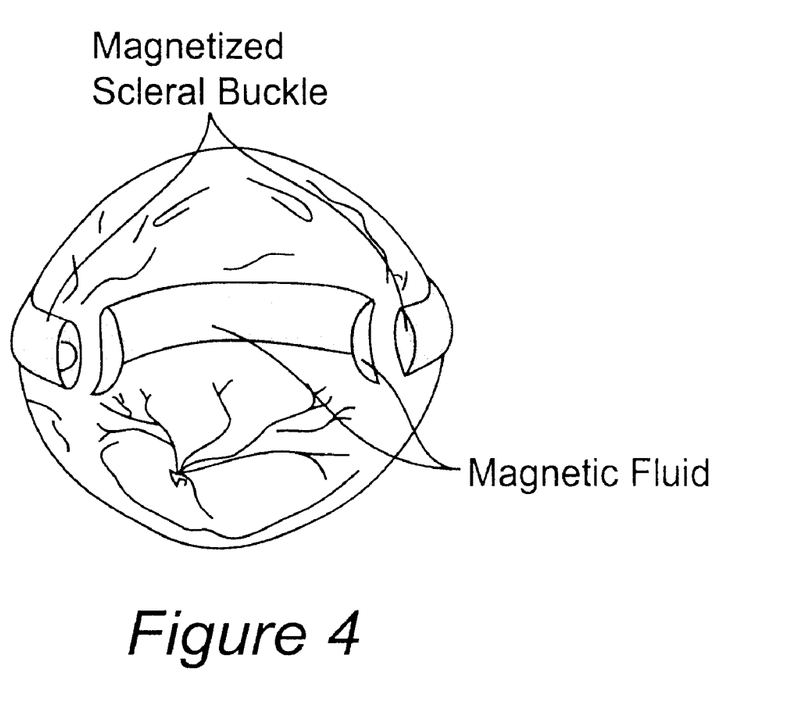
FIG. 4 is a perspective view of a 360 degree ring of magnetic fluid formed in apposition to the retinal periphery, as a result of applying the method in accordance with the present invention.

An encircling magnetized scleral buckle and magnetic fluid produces a 360 degree ring of magnetic fluid in apposition to the retinal periphery. Furthermore, the central vitreous cavity is free of magnetic fluid, and there is no contact between the magnetic fluid and the lens, anterior chamber structures, and macula.

EXAMPLE 1

Preparation of Scleral Buckle

Neodymium/iron particles are dispersed in polysiloxanes with acetoxy functional groups which condense in the presence of atmospheric moisture at low temperature to yield crosslinked polydimethylsiloxane elastomers. These are molded in an appropriate configuration for scleral buckling elements, having about 10% by volume magnetic particles.

EXAMPLE 2

(PDMS-b-PCPMS-b-PDMS) Triblock Copolymer Dispersion Stabilizers

Reagents

Dichloromethane (Baxter) was washed twice with concentrated sulfuric acid, then with water until neutral. Subsequently, it was pre-dried with anhydrous magnesium sulfate and distilled from phosphorus pentoxide. Hexamethylcyclotrisiloxane (General Electric Co.) was stirred over calcium hydride powder at 80° C. for 12 h, then distilled into a dry flask where it was diluted with anhydrous dichloromethane. Tetrahydrofuran (E.M. 99.5%), Triethylene glycol dimethyl ether (TEGDME, Aldrich, 99%) were refluxed over sodium/benzophenone until the solution was deep purple, then they were distilled just prior to use. Trimethylchlorosilane (99+%, Aldrich) was treated with anhydrous potassium carbonate and distilled before use. Allyl cyanide (98%, Aldrich) was dried with 4 Å molecular sieves prior to distillation. Butyllithium (1.6 M in hexane, Aldrich) was used as received. Toluene (Fisher) was stirred over calcium hydride for 24 h and distilled just prior to use. Diphenylsilanediol (97%, Aldrich) was purified by recrystallization in a mixture of methyl isobutyl ketone and chloroform. Diphenylmethane (99%, Aldrich) was distilled over calcium hydride.

(3-Cyanopropyl)methylsiloxane Cyclics

A dry 500 ml two-neck flask was equipped with a condenser and a magnetic stirring bar. A drying tube containing Drierite was attached. To the flask was charged 50 ml (49 g, 0.20 mol) $D_4H$ (Dow Corning), 100 ml purified toluene, 80 ml (66 g, 1 mol) purified allyl cyanide and 0.2 ml Pt(0)-1,3-divinyl-1,1,1,3,3-tetramethyldisiloxane (Huls America). The mixture was refluxed for 24 h: then toluene was removed and $D_4CN$ recovered at 250–280° C./0.5 Torr (yield 130 g, 90%).

Dilithium Diphenylsilanediolate

Many reagents in this experiment are very sensitive to moisture, so all flasks and reactors were carefully dried, syringes or double-tip needles were used to transfer liquids and suspensions, and reactions were carried out in nitrogen atmosphere and bubblers were used to control inner pressure.

A 250 ml one-neck flask with magnetic stirrer was charged with 100 ml tetrahydrofuran, 14 ml diphenylmethane (0.083 mol) and 43 ml 1.6 M butyllithium solution (0.0688 mol). After 2 h, a dark red solution was obtained. A solution of diphenylsilanediol was prepared by dissolving 10 g recrystallized diphenylsilanediol into 40 ml anhydrous THF. The diphenylmethyl lithium solution was titrated with the diphenylsilanediol solution until the mixture was colorless. To have a slight excess diphenymethyl lithium, the mixture was back titrated with diphenylmethyl lithium until pale red. The reaction mixture was kept undisturbed for 24 h to allow dilithium diphenylsilanediolate to precipitate from the solution. Next, the suspension was transferred to centrifugation tubes. Dilithium diphenylsilanediolate was washed with THF once, dichloromethane twice. All separation was done by centrifugation while redispersion was done by ultrasonic agitation. Finally, dilithium diphenylsilanediolate was preserved as a suspension in dichloromethane. The molecular weight of the prepared dilithium diphenylsilanediolate determined by titration was 228±15 g/mol (theoretically 228 g/mol). Analyses of dilithium diphenylsilanediolate was performed using its derivative 1,1,1,3,3,3-hexamethyl-2,2-diphenylsiloxane, which was obtained by the reaction of trimethylchlorosilane with dilithium diphenylsilanediolate. $^{29}Si$ NMR (singlet $\delta$10 ppm, 2 Si from $Me_3SiO$—; singlet $\delta$-48 ppm, 1 Si from —$OSiPh_2O$—).

Lithium Silanolate Endcapped PCPMS Macroinitiators

Lithium silanolate endcapped PCPMS macro-initiators were prepared by equilibration of mixtures of (3-cyanopropyl) methylcyclosiloxanes with dilithium diphenylsilanediolate. The molecular weights were controlled by the ratios of the monomer to the initiator, so dilithium diphenylsilanediolate functions as both catalyst and chain stopper. Given below is a procedure for preparation of a 2.5 k g/mol macroinitiator. Other macroinitiators were prepared similarly but with different ratios of the monomer to the initiator.

TABLE 1

RECIPES FOR 2.5 k, 4 k, 8 k PCPMS MACROINITIATORS

| Monomer:initiator (g/mol) | 2.5 k | 4 k | 8 k |
|---|---|---|---|
| Weight of monomer (g) | 10 | 10 | 10 |
| Moles of $Li_2O_2SiPh_2$ | 0.004 | 0.0025 | 0.00125 |

Equilibrium conversion of the cyclics is ≈ 73%.

A one-neck flask with magnetic stirrer was capped with a septum, flame-heated and flushed with dry nitrogen to remove moisture. The flask was charged with 10 ml (~10 g) distilled (3-cyanopropyl) methylcyclosiloxane mixture and 0.004 mol dilithium diphenylsilanediolate (2.5 k g/mol). The dilithium diphenylsilanediolate was added as suspensions in dichloromethane. After the reactants had mixed for 2 h at room temperature, dichloromethane was removed by vacuum distillation. Then the flask was placed in an isothermal oil bath (T~100° C.) for equilibration. The 2.5 k g/mol PCPMS equilibrated macroinitiator was obtained after 48 h.

Polydimethylsiloxane-b-Poly(3-cyanopropyl) methylsiloxane-b-Polydimethylsiloxane Triblock Copolymers (PDMS-b-PCPMS-b-PDMS)s were prepared by living polymerizations of $D_3$ initiated by lithium silanolate endcapped PCPMS macroinitiators. Given below is a procedure for a 2.5 k-2.5 k-2.5 k triblock polymer. Other polymers were similarly prepared. Conversion of $D_3$ for each system was measured by $^{29}Si$ NMR.

A 2.5 k g/mol PCPMS macroinitiator (10 g) was dissolved in 60 ml dry dichloromethane, and the macroinitiator solution was transferred to a dry 250 ml one-neck flask which contained 140 ml $D_3/CH_2Cl_2$ solution (including 20 g $D_3$), 20 ml anhydrous TEGDME and a magnetic stirrer. The mixture was stirred at room temperature for about 48 h, then the reaction was terminated with 1.5 ml purified trimethylchlorosilane. $^{29}Si$ NMR indicated that the conversion of $D_3$ at this time was around 85%. Next, solvent and residual trimethylchlorosilane were removed from the reaction mixture by distillation, the polymer was dissolved in a small amount of chloroform and precipitated into 200 ml methanol to remove nitrile containing cyclics. The triblock copolymer was recovered by decantation, then it was further dried in a vacuum oven at 80° C. for 24 h.

EXAMPLE 3

(PDMS-b-PCPMS-b-PDMS) Triblock Copolymer Dispersion Stabilizers

An alternative procedure for preparing PDMS-b-PCPMS-b-PDMS triblock copolymer dispersion stabilizers is outlined in Scheme 4. $D_4CN$ is prepared as in previous experiments by the hydrosilylation of $D_4H$ with allyl cyanide. However, the lithium silanolate capped PCPMS macroinitiators are prepared by equilibrium polymerization of $D_4CN$ with LiOH. Triblock copolymers, PDMS-b-PCPMS-b-PDMSs, are obtained by kinetically controlled polymerization of $D_3$ using the lithium silonate capped PCPMS macroinitiators.

EXAMPLE 4

Preparation of Magnetic Fluid Using Cobalt

The procedure for magnetic fluid preparation is outlined below in Scheme 5. A quantity of stabilizer, sufficient to completely encapsulate the cobalt particle is added with toluene to a reaction vessel. Cobalt carbonyl is added and thermally decomposed in situ to form the cobalt metal particles. The fluid is then placed through an initial screening process, to test for precipitation/destabilization in a magnetic field and TEM measurements of particle size, and then transferred to an appropriate carrier fluid.

Scheme 5

EXAMPLE 5
Preparation of Cobalt-Based Magnetic Fluids

A series of copolymers was prepared with varied block lengths as shown in Table 2. Stabilizers 1, 3 and 5 were prepared by the method in Example 2, as depicted in Scheme 3. Stabilizer 4 was prepared by the method in Example 3, as depicted in Scheme 4. Independent samples of stabilizer 2 were prepared by both methods.

TABLE 2

Copolymer Series

| STABILIZER | PDMS-PCPMS-PDMS |
|---|---|
| 1 | 5,500-1,800-5,500 g/mole |
| 2 | 15,200-1,800-15,200 g/mole |
| 3 | 7,900-5,000-7,900 g/mole |
| 4 | 5,530-5,000-5,530 g/mole |
| 5 | 16,600-5,000-16,600 g/mole |

Block length $M_n$ in g/mole determined by GPC, and $^1H$, $^{29}Si$ NMR

EXAMPLE 6
Preparation of Magnetic Fluid with Stabilizer

A reaction vessel containing 20 mL of toluene was charged with 0.824 g of stabilizer 3 as prepared in Example 5. Once the stabilizer dissolved, 5 g of cobalt carbonyl was added with stirring. The reaction mixture was heated to 45° C. and maintained for 1 hour. After this initial stage of reaction, the temperature was increased to an oil bath reading of 100° C. and maintained until CO evolution ceased. The fluid was cooled to room temperature and passed through the initial screening process. A 2 mL portion of the fluid was removed and added to 1 mL of $D_4$ carrier fluid (200% concentrated). The toluene was removed by rotary evaporation, monitoring by IR.

EXAMPLE 7
Preparation of Magnetic Fluid with Stabilizer

A reaction procedure similar to that described in example 6 was performed with the following changes. A 3.5 g portion of stabilizer 2 as prepared in Example 5 was employed; this is double the quantity calculated to be necessary for complete coverage of the particles. The reaction was allowed to proceed at 45° C. for 30 min and was then heated to 135° C. and maintained until CO evolution ceased. The resulting fluid was placed through the initial screening tests. A 2 mL portion of the fluid was transferred to a 1 mL volume of 2,000 g/mole PDMS carrier liquid (200% concentrated) by the procedure described in example 1. Magnetization measurements indicate a saturation magnetization of 12.4 emu/g of fluid and transmission electron microscopy showed an average particle size of 17 nm diameter. Magnetization measurements were also obtained on a portion of this fluid concentrated by 500% and values of 20.0 emu/g were obtained for the saturation magnetization.

EXAMPLE 8
Preparation of Magnetic Fluid with Stabilizer

The reaction procedure described in example 7 was followed with the following changes. A 13.8 g portion of stabilizer was employed; this value is 8 times what was calculated to be necessary to cover the cobalt particles produced. The resulting fluid was concentrated by rotary evaporation until no toluene remained, monitoring by IR. Preliminary screening tests were passed. A saturation magnetization of 22.4 emu/g of fluid was obtained.

EXAMPLE 9
Preparation of a Nickel-Based Magnetic Fluid with Stabilizer

The reaction procedure for preparing nickel based magnetic fluids is similar to those for preparing cobalt based fluids except that di(1,5-cyclooctadienyl)nickel is used as the organometallic precursor for the fluid. A reaction vessel containing 20 mL of toluene is charged with 0.824 g of stabilizer 3 as prepared in Example 5. Once the stabilizer is dissolved, 5 g of di(1,5-cyclooctadienyl)nickel is added with stirring. The reaction mixture is heated to 45° C. and maintained for 1 hour. After this initial stage of reaction, the temperature is increased to an oil bath reading of 100° C. and maintained until the stabilizer had displaced the 1,5-cyclooctadiene ligands on the nickel. The fluid is cooled to room temperature and passed through the initial screening process. A 2 mL portion of the fluid is removed and added to 1 mL of 2000 Mn polydimethylsiloxane carrier fluid (200% concentrated). The toluene is removed by rotary evaporation, monitoring by IR.

What is claimed:

1. A method for treating retinal detachment in an eye comprising:

a) inserting an effective amount of a stabilized composition comprising magnetic particles and a block copolymer stabilizer in a polysiloxane medium, wherein the stabilizer comprises at least one cyano-containing polysiloxane block capable of chelating the metal particles, and at least one end block comprising a polysiloxane which is compatible with the medium; and b) applying a magnetized scleral buckle to said eye.

* * * * *